United States Patent
Case et al.

(10) Patent No.: US 8,403,977 B2
(45) Date of Patent: Mar. 26, 2013

(54) SELF-ORIENTING DELIVERY SYSTEM

(75) Inventors: Brian C. Case, Lake Villa, IL (US); Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 513 days.

(21) Appl. No.: 11/800,292

(22) Filed: May 4, 2007

(65) Prior Publication Data

US 2007/0260263 A1    Nov. 8, 2007

Related U.S. Application Data

(60) Provisional application No. 60/746,378, filed on May 4, 2006.

(51) Int. Cl.
- *A61F 2/06* (2006.01)
- *A61F 2/84* (2006.01)
- *A61M 29/02* (2006.01)

(52) U.S. Cl. .................. 623/1.11; 606/194; 623/2.11

(58) Field of Classification Search .................. 623/1.11; 606/194

See application file for complete search history.

(56) References Cited

U.S. PATENT DOCUMENTS

| | | | |
|---|---|---|---|
| 2,649,092 A | 8/1953 | Wallace | |
| 3,583,391 A | 6/1971 | Cox et al. | |
| 4,790,812 A | 12/1988 | Hawkins | |
| 5,397,311 A | 3/1995 | Walker | |
| 5,509,900 A | 4/1996 | Kirkman | |
| 5,534,007 A | 7/1996 | St. Germain | |
| 5,643,171 A | 7/1997 | Bradshaw | |
| 5,658,301 A | 8/1997 | Lemaitre | |
| 5,718,684 A | 2/1998 | Gupta | |
| 5,769,821 A | 6/1998 | Abrahamson | |
| 5,779,670 A | 7/1998 | Melman et al. | |
| 5,792,114 A | 8/1998 | Fiore | |
| 5,797,952 A * | 8/1998 | Klein | ............... 623/1.12 |
| 5,938,582 A | 8/1999 | Ciamacco | |
| 6,007,521 A | 12/1999 | Melman | |
| 6,071,263 A | 6/2000 | Kirkman | |
| 6,117,386 A | 9/2000 | Stiger | |
| 6,168,617 B1 | 1/2001 | Blaeser et al. | |
| 6,338,735 B1 | 1/2002 | Stevens | |
| 6,383,206 B1 | 5/2002 | Gillick | |
| 6,447,530 B1 | 9/2002 | Ostrovsky | |

(Continued)

FOREIGN PATENT DOCUMENTS

| | | |
|---|---|---|
| CA | 2403030 | 3/2003 |
| WO | WO-01/26726 | 4/2001 |

(Continued)

OTHER PUBLICATIONS

European Patent Office Communication for European patent application No. 07/794571.5 mailed Feb. 25, 2011.

*Primary Examiner* — Kathleen Holwerda
*Assistant Examiner* — Sarah W Aleman
(74) *Attorney, Agent, or Firm* — Buchanan Nipper (57) ABSTRACT

Delivery systems for delivering and deploying expandable intraluminal medical devices within a body vessel are provided. A portion of the delivery system that includes the expandable intraluminal medical device orients itself about an axis based on characteristics of the body vessel, such as the relative orientation of major and minor axes of the vessel. This allows the intraluminal medical device to be deployed in the vessel in a desired orientation relative to the vessel. Embodiments can be used with any suitable intraluminal medical device, including valve devices, stents, drug-coated stents, filters, and other suitable devices. Methods of delivering and deploying intraluminal medical devices are also described.

10 Claims, 4 Drawing Sheets

U.S. PATENT DOCUMENTS

| | | |
|---|---|---|
| 6,450,988 B1 | 9/2002 | Bradshaw |
| 6,485,500 B1 * | 11/2002 | Kokish et al. ............ 606/194 |
| 6,491,662 B1 | 12/2002 | Liprie |
| 6,500,182 B2 | 12/2002 | Foster |
| 6,508,833 B2 | 1/2003 | Pavcnik |
| 6,558,349 B1 | 5/2003 | Kirkman |
| 6,629,987 B1 | 10/2003 | Gambale |
| 6,679,860 B2 | 1/2004 | Stiger |
| 6,692,484 B1 | 2/2004 | Karpiel |
| 6,695,858 B1 | 2/2004 | Dubrul |
| 6,918,929 B2 * | 7/2005 | Udipi et al. ............ 623/1.42 |
| 6,932,829 B2 * | 8/2005 | Majercak ................ 606/198 |
| 2001/0039450 A1 * | 11/2001 | Pavcnik et al. ........ 623/1.24 |
| 2001/0044648 A1 | 11/2001 | Wolinsky et al. |
| 2002/0068866 A1 | 6/2002 | Zikorus |
| 2003/0032977 A1 | 2/2003 | Brady |
| 2003/0050694 A1 | 3/2003 | Yang |
| 2003/0055483 A1 * | 3/2003 | Gumm ................... 623/1.11 |
| 2004/0087965 A1 | 5/2004 | Levine et al. |
| 2004/0087996 A1 | 5/2004 | Gambale |
| 2004/0225322 A1 | 11/2004 | Garrison |
| 2005/0125050 A1 | 6/2005 | Carter |
| 2005/0149096 A1 | 7/2005 | Hilal et al. |
| 2005/0171592 A1 * | 8/2005 | Majercak ................ 623/1.11 |
| 2005/0228479 A1 | 10/2005 | Pavcnik et al. |
| 2006/0058647 A1 | 3/2006 | Strommer et al. |
| 2006/0058865 A1 | 3/2006 | Case et al. |
| 2006/0135961 A1 | 6/2006 | Rosenman et al. |
| 2007/0055326 A1 | 3/2007 | Farley et al. |
| 2007/0055327 A1 | 3/2007 | Esch et al. |
| 2007/0067021 A1 | 3/2007 | Haverkost et al. |

FOREIGN PATENT DOCUMENTS

| | | |
|---|---|---|
| WO | WO-01/83017 | 11/2001 |
| WO | WO-2004/082530 | 9/2004 |
| WO | WO-2006/028821 | 3/2006 |

* cited by examiner

FIG. 7

SELF-ORIENTING DELIVERY SYSTEM

CROSS REFERENCE TO RELATED APPLICATION

This application claims priority to U.S. Provisional Application Ser. No. 60/746,378, filed on May 4, 2006. The entire contents of this provisional application are hereby incorporated by reference into this disclosure.

FIELD

The invention relates generally to the field of medical devices. Particular embodiments of the invention can be applied to the field of delivery systems for deploying intraluminal medical devices within a body vessel.

BACKGROUND

Intraluminal medical devices are commonly used in a variety of medical procedures. For example, stents are commonly used to provide intraluminal support to a body vessel, such as a coronary artery. Minimally invasive techniques are frequently used to delivery such medical devices to a desired point of treatment and to deploy the medical device at the point of treatment. In these techniques, a delivery system is used to carry the intraluminal medical device through a body vessel and to the point of treatment. Once the point of treatment is reached, the intraluminal medical device is deployed from the delivery system, which is subsequently withdrawn from the point of treatment and, ultimately, the body vessel.

Body vessels are typically soft and elastic in nature. As a result, body vessels have a variable cross-sectional shape and frequently change between various cross-sectional configurations depending on various factors, including current body activity and position. For example, veins frequently exhibit a substantially circular cross-sectional shape when the body is ambulatory but exhibit a substantially ovoid cross-sectional shape when the body is in a supine or prone position. As a result, most body vessels are dynamic and can be viewed as having major and minor cross-sectional axes.

Some intraluminal medical devices include a functional mechanism that is sensitive to orientation within a body vessel relative to one or more cross-sectional axes of the body vessel. An intraluminal medical device may include a functional mechanism that may not perform entirely as desired if the functional mechanism is not positioned in a particular orientation relative to one or more of the cross-sectional axes of the body vessel following deployment. For example, some prosthetic valve devices include a valve orifice having a major and a minor axis. For some valve devices, it may be desirable to substantially align the major axis of the valve orifice with the major axis of the vessel when it is in a configuration having a substantially ovoid cross-sectional shape, such as when the patient is in a supine position during the implantation procedure. In some circumstances, the valve device may not function as desired if this alignment is not achieved, particularly if the major axis of the valve orifice is grossly misaligned with the major axis of the body vessel. The leaflets of a valve device that is mis-oriented in this manner may be obstructed or otherwise affected by such orientation. Furthermore, other types of intraluminal medical devices, such as drug-coated stents, may include a functional mechanism, such as a localized deposit of a bioactive, that should be positioned immediately adjacent a particular circumferential portion of a vessel wall, such as a point at which a plaque has developed or has been deposited, to achieve a desired treatment outcome.

Positioning intraluminal medical devices within a body vessel in a manner that achieves such desired orientations relative to the body vessel can be difficult. During conventional percutaneous delivery and deployment procedures, the intraluminal medical device is deployed from a delivery system at a remote location within the body vessel. Monitoring the orientation relative to the body vessel is often difficult with conventional delivery systems, even with sophisticated imaging equipment and techniques, and adjustment of the orientation by rotating a conventional delivery system about a lengthwise axis is an imprecise approach that is viewed by many skilled artisans as difficult to control and ineffective. Prior art delivery systems may not provide a desirable system for deploying such intraluminal medical devices in a manner that achieves the desired orientation. Accordingly, there is a need for improved delivery systems and methods of delivering intraluminal medical devices.

SUMMARY OF EXEMPLARY EMBODIMENTS

Delivery systems for implanting an intraluminal medical device at a point of treatment within a body vessel are described. A delivery system according to exemplary embodiments includes a dilator having a main body and a head member that are connected to each other in a manner that allows the head member to rotate about a longitudinal axis of the head member while the main body remains relatively static. The head member includes a mounting region that receives an intraluminal medical device and one or more connected orientation members adapted to engage a body vessel and effect rotation of the head member—and the associated intraluminal medical device—during advancement of the head member within a portion of a body vessel.

Additional understanding can be obtained with review of the detailed description of exemplary embodiments, appearing below, and the appended drawings illustrating exemplary embodiments.

DETAILED DESCRIPTION OF EXEMPLARY EMBODIMENTS

The following detailed description and the appended drawings describe and illustrate various exemplary embodiments of the invention. The description and drawings are exemplary in nature and are provided to enable one skilled in the art to make and use one or more embodiments of the invention. They are not intended to limit the scope of the invention, or its protection, in any manner.

Figure 1:
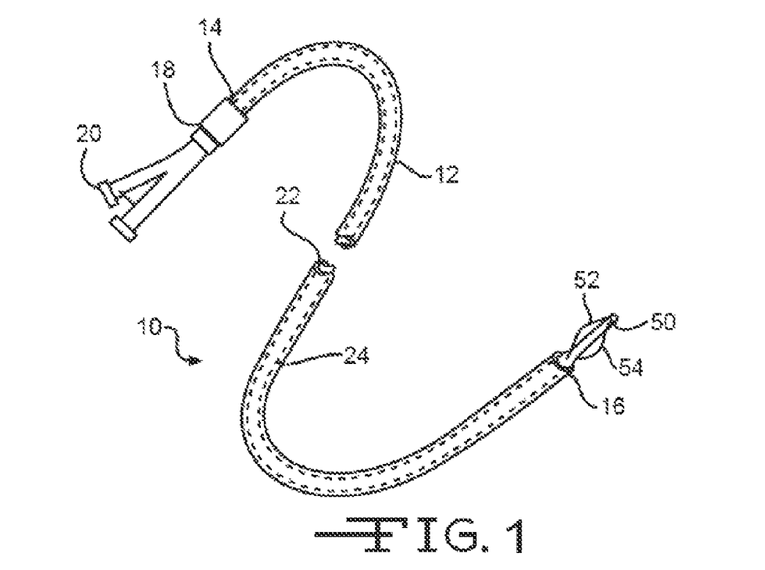
FIG. 1 is a perspective view, partially broken away, of a delivery system according to a first exemplary embodiment.
Figure 2:
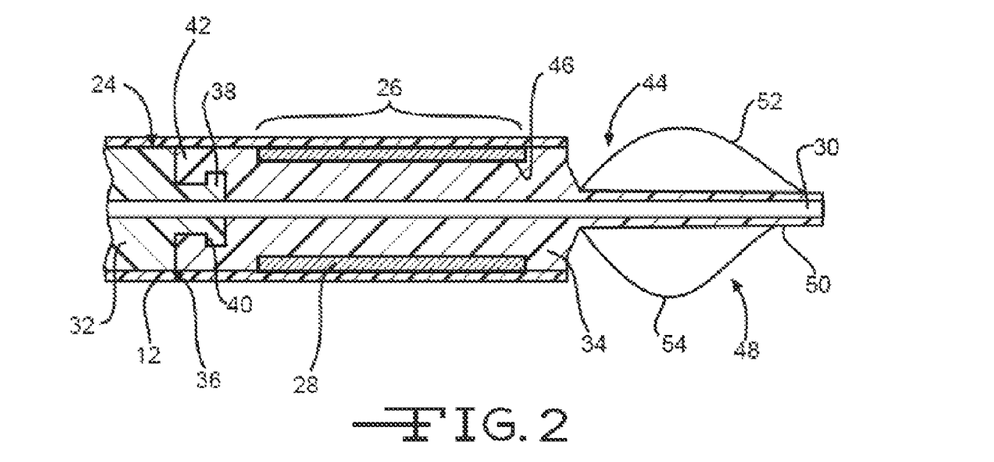
FIG. 2 is an enlarged, sectional view of the distal end of the delivery system illustrated in FIG. 1.

FIGS. 1 and 2 illustrate a delivery system, generally indicated at 10, according to a first exemplary embodiment. The delivery system 10 includes an elongate tubular member 12, such as a conventional sheath member used in delivery systems known in the art, having proximal 14 and distal 16 ends. The proximal end 14 may include one or more connectors 18, ports 20, or other accessory components for use with the delivery system 10. A lumen 22 extends through the elongate tubular member 12 from the proximal end 14 to the distal end 16. A dilator 24 is disposed within the lumen 22 of the elongate tubular member 12 and defines a mounting region 26 on which an expandable intraluminal medical device 28 is disposed. The elongate tubular member 12 is initially disposed over the mounting region 26 and the expandable intraluminal medical device 28 but can be retracted or otherwise manipulated in a manner that exposes the intraluminal medical device 28 for deployment at a point of treatment within a body vessel.

In this embodiment, the dilator 24 is slidably disposed within the lumen 22 of the elongate tubular member 12 and defines a wireguide lumen 30 through which a conventional wireguide (not illustrated) can be disposed, allowing the dilator 24, and the delivery system 10, to be advanced over a wireguide that has been previously placed within a body vessel.

Indeed, it is explicitly recognized by the inventors that the various types of delivery systems can be constructed as embodiments of the invention, including over-the-wire, rapid exchange, short wire, intraductal exchange, and other delivery system types known in the art. For example, in an over-the-wire embodiment, the wireguide lumen 30 extends along the entire length of the dilator 24. Alternatively, in a rapid exchange embodiment, the lumen 30 extends along only a portion of the dilator 24 in a manner that facilitates rapid exchange of components, as is known in the art.

As best illustrated in FIG. 2, the dilator 24 includes a main body 32 and a head member 34. The head member 34 substantially comprises the distal end of the dilator 24 and includes the mounting region 26 on which the intraluminal medical device 28 is disposed. The main body 32 and the head member 34 are rotatably connected at connection 36. The connection 36 enables the head member 34 to rotate circumferentially about a lengthwise axis of the head member substantially independent of any circumferential rotation of the main body 32. The connection 36 can comprise any suitable means for rotatably connecting two members capable of sharing substantially the same lengthwise axis.

FIG. 2 illustrates one exemplary structure for the connection 36. In this embodiment, the main body 32 defines a projection 38 that is received by a socket 40 defined by the head member 34. The projection 38 and socket 40 advantageously fit together in a manner that permits rotation of the head member 34 relative to the main body 32 but doesn't permit axial disconnection of these elements. The connection 36 advantageously includes a degree of play between the elements to facilitate navigation of the dilator 24, and indeed the delivery system 10, through a body vessel, such as through curved and other tortuous sections of the vessel. The extent of play incorporated into any particular embodiment of the invention will depend on various considerations, including the desired ease of rotation of the head member 34, the desired trackability of rotation of the head member 34 with rotation of the main body 32, the relative tortuosity of the body vessels within which the embodiment is intended to be used, and other considerations.

In an alternate embodiment, the head member can comprise a tubular member disposed circumferentially around the distal end of the dilator 24 in a manner that allows the head member to at least partially rotate about the distal end as described herein. In this embodiment, the head member is disposed around a portion of the dilator, and share a lengthwise axis. Similar to the illustrated embodiment, the mounting region 26 is formed on the external surface of the head member and the intraluminal medical device is disposed on the mounting region 26. In this embodiment, a suitable connection that permits such rotation of the head member about the distal end of the dilator 24 can advantageously be used. A connection comprising a mating projection and socket, formed on the distal end of the dilator 24, is considered suitable.

The wireguide lumen 30 of the dilator 24 extends through both the main body 32 and the head member 34 in a substantially continuous manner to facilitate advancement of the dilator 24, and the delivery system 10 as a whole, over a previously placed wireguide according to conventional percutaneous techniques.

The head member 34 has a proximal portion 42 and a distal portion 44. The proximal portion 42 includes the structure of the head member 34 that participates in the connection 36, such as socket 40 shown in FIG. 2. The proximal portion 42 also includes the mounting region 26 on which the intraluminal medical device 28 is disposed. The mounting region 26 can simply be a portion of the surface of the proximal portion 42 or, alternatively, can comprise a recessed section 46 of the proximal portion 42 that is adapted to receive the intraluminal medical device 28, as illustrated in FIG. 2.

To facilitate rotation of the head member 34 and the associated intraluminal medical device 28 while positioned adjacent an inner surface of the elongate tubular member 12 (e.g., when in a "sheathed" configuration), it may be advantageous to secure the intraluminal medical device 28 to the mounting region 26 or other portion of the head member 34 using an appropriate means for securing one item to another. Any suitable structure can be used for the means for securing, including projections that protrude into and create a friction fit with a cell or other suitable structure of the intraluminal medical device 28, one or more adhesive connections, and frangible mechanical connections. The structure chosen for any particular embodiment should be selected to not only provide a connection between the head member 34 and the intraluminal medical device 28 that permits coordinated rotation of the head member 34 and the intraluminal medical device 28 while the elongate tubular member 12 is disposed about the intraluminal medical device 28, but also to be sufficiently fragile to enable the intraluminal medical device 28 to expand and disengage from the means for securing when the elongate tubular member 12 is retracted from a position about the mounting region 26 to effect deployment of the intraluminal medical device 28. Exemplary structures and other suitable means for securing are described in commonly-owned U.S. Patent Application Publication No. 2006/0058865, entitled DELIVERY SYSTEM WITH CONTROLLED FRICTIONAL PROPERTIES, the entire contents of which are hereby incorporated by reference into this disclosure.

Figure 4:
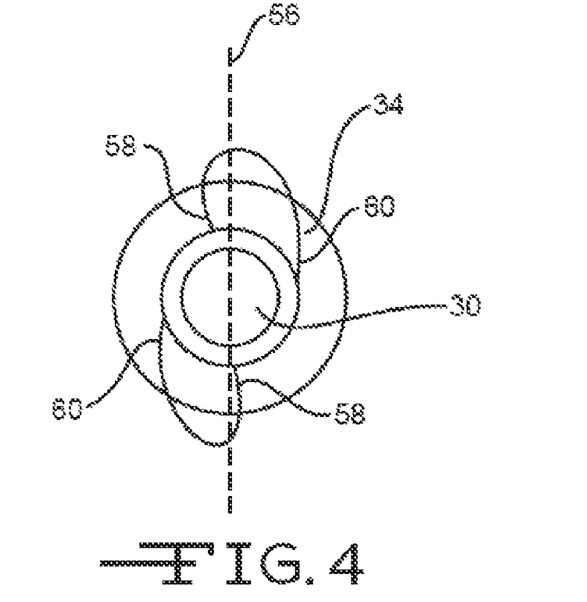
FIG. 4 is an end view of the distal end of the delivery system illustrated in FIG. 1 and FIG. 2.

As best illustrated in FIGS. 2 and 4, the distal portion 44 of the head member 34 includes an orienting section 48 for orienting the head member 34 as it is advanced through a portion of a body vessel. The orienting section 48 includes a support member 50 and at least one orienting member 52 extending therefrom. The support member 50 extends from the proximal portion 42 of the head member 34 and advantageously has an outer diameter less than the outer diameter of the mounting region 26 and/or the proximal portion 42 of the head member 34.

The orienting member 52 advantageously comprises a elongate resilient member, such as a strand formed of wire, plastic or other suitable material. The orienting member(s) 52 in any given embodiment can be formed from any suitable resilient material(s), including stainless steel or an elastic alloy, such as nitinol, to permit the orienting member to be collapsed and collected into a sheath. Furthermore, the orienting members 52 may be coated with any suitable coating or other material, including lubricious and/or bioactive coatings. The orienting members may be removably or permanently attached to the support member 50.

The orienting member 52 may be similar in construction to the elongate resilient members of an expandable basket as is known in the art. A description of exemplary expandable basket structures is provided in U.S. Patent Application Publication No. 2004/0225322 filed by Garrison et al. for DELIVERY SYSTEMS AND METHODS FOR DEPLOYING EXPANDABLE INTRALUMINAL MEDICAL DEVICES, the entire disclosure of which is expressly incorporated into this disclosure by this reference. Expandable basket structures are known in the retrieval art and are commonly used to remove an object, such as a stone or other undesirable object, from a body cavity. Expandable basket structures have not been used, however, to orient an intraluminal medical device within a body vessel during advancement through a portion of a body vessel as described herein.

In the embodiment shown in FIGS. 1, 2, and 4, the orienting section 48 includes two orienting members 52, 54 arranged in an opposing relationship and extending outwardly from the support member 50 to define a major axis 56 of the distal portion 44 of the head member 34. In use, the orienting members 52, 54 seek the major axis of the body vessel, due to their expandable nature, as the distal portion 44 of the head member 34 is advanced through a portion of a body vessel. To facilitate the orienting members 52, 54 conforming to the contour of the body vessel, each of the orienting members 52, 54 are advantageously attached to the support member 50 with a proximal end 58 angularly offset from a distal end 60. As best illustrated in FIG. 4, the proximal end 58 is advantageously offset approximately 90 degrees from the distal end 60. However, it is expressly contemplated that the proximal end 58 of any given orienting member 52, 54 may be offset from the corresponding distal end 60 by any suitable angle from between 0 and 360 degrees. Thus, the proximal ends 58 may be longitudinally aligned with the distal ends 60 with the orienting members 52, 54 extending along one side of the support member 50 or with the orienting members 52, 54 having been rotated or spiraled about the support member 50 so long as a major axis 56 is formed for the distal portion 44 of the head member 34.

It is noted that an ancillary device that includes orienting members in lieu of orienting members 52, 54 that are attached to the head member 34 can be used in embodiments of the invention. In these alternate embodiments, an ancillary device, such as the wire-formed members that include spacing members described in U.S. Patent Application Publication No. 2004/0225322, the entire contents of which are hereby incorporated by reference into this disclosure, can be passed through the wireguide lumen 30 until the spacing members emerge from the head member 34 of the dilator 24. The spacing members in this alternate embodiment can be configured to sufficiently engage the head member 34 upon emerging therefrom such that the head member 34 rotates with the rotation of the spacing members, as described above relative to the previously described and illustrated embodiment.

Any suitable number of orienting members can be used and the number chosen for a specific delivery system according to an embodiment of the invention will depend on several considerations, including the nature and type of the body vessel in which the delivery system is intended to be used. It is expected that the inclusion of two, three, or four orienting members would provide desirable behavior of the delivery system in a body vessel, but any suitable number can be included. Furthermore, it is not necessary that each orienting member include the same or similar offset as the other orienting member(s) included in a particular delivery system, although it is expected that the inclusion of two or more orienting members that have substantially the same offset between their respective proximal and distal ends would produce desired behavior of the delivery system in a body vessel.

Figure 5:
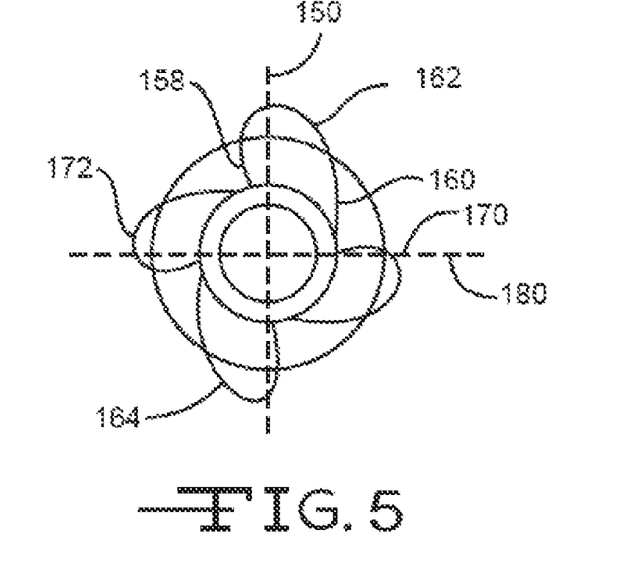
FIG. 5 is an end view of the distal end of a delivery system according to an alternate embodiment.

FIG. 5 illustrates the distal end of a delivery system according to an alternate embodiment. The delivery system according to this embodiment is similar to the embodiment described above and illustrated in FIG. 1, FIG. 2, and FIG. 4, except as described below. In this embodiment, the head member 134 includes a first pair of orienting members 160, 162 that are disposed substantially opposite one another and are sized and arranged to define a major axis 150 for the distal portion 144 of the head member 134. The head member 134 also includes a second pair of orienting members 170, 172 that are disposed substantially opposite one another and are sized and arranged to define a minor axis 180 for the distal portion 144 of the head member 134. FIG. 5 illustrates the proximal end 156 of each orienting member as offset by approximately 90 degrees from the corresponding distal end 158; however, the proximal ends 156 may be offset from the distal ends 158 at any suitable angle from between 0 and 360 degrees so long as the desired major axis 150 and minor axis 180 are formed for the distal portion 144 of the head member 134.

Referring again to the embodiment illustrated in FIGS. 1, 2 and 4, if it is desired to orient the intraluminal medical device 28 in a particular manner in the body vessel, the intraluminal medical device 28 is positioned on the mounting region 26 with the intraluminal device 28 aligned with the major axis 56 of the distal portion 44 of the head member 34 in such a manner that a desired portion, such as a functional mechanism of the intraluminal medical device 28, is aligned with the major axis 56. For example, if the intraluminal medical device comprises a valve device and it is desired to deploy the valve device in a manner that positions the valve orifice substantially across a major axis of a body vessel, the valve device is positioned on the mounting region 26 with the valve orifice substantially aligned with the major axis 56 of the distal portion 44 of the head member 34, as defined by the appropriate orienting members 52, 54. Also, if the intraluminal medical device 28 comprises a stent having a localized deposit of a bioactive agent and it is desired to deploy the stent in a manner that positions the bioactive agent adjacent a portion of the vessel wall that is on the major or minor axis of the body vessel, the stent is positioned on the mounting region 26 with the bioactive agent substantially aligned with the major 56 or minor 18 axis of the distal portion 44 of the head member 34, as desired and as defined by the appropriate orienting members 52, 54. To facilitate placement of the intraluminal medical device on the mounting region 26 in this manner, the head member 34 may include suitable markings, such as registration markings, to aid in orienting the intraluminal device 28 on the mounting region 26.

In all embodiments, the intraluminal medical device 28 can comprise any suitable intraluminal medical device, including both self-expandable devices and those that require the input of an external force to effect expansion, such as balloon expandable intraluminal medical devices. If such devices are used, the dilator should be modified appropriately to accommodate the need for an external force to effect expansion, such as by including a balloon and an inflation lumen as is known in the art.

The specific type of intraluminal medical device used in a specific delivery system according to a particular embodiment of the invention will depend on several considerations, including the type of vessel in which the delivery system is being used and the nature of the clinical situation for which the delivery system has been selected. Examples of suitable types of intraluminal medical devices that can be used with delivery systems according to various embodiments of the invention include self-expandable stents, valve devices that include a self-expandable support frame, such as prosthetic valves for implantation in a vein (prosthetic venous valves) or in a heart vessel and/or chamber (prosthetic heart valves), self-expandable filters, distal protection devices, vessel occluders, and other self-expandable devices. Suitable self-expandable medical devices for use with delivery systems according to the invention include those described in U.S. Pat. No. 6,200,336 to Pavcnik et al. for a MULTIPLE-SIDED INTRALUMINAL MEDICAL DEVICE; U.S. application for patent Ser. No. 10/642,372 of Pavcnik et al. for an IMPLANTABLE VASCULAR DEVICE, filed on Aug. 15, 2003; and U.S. application for patent Ser. No. 10/828,716 of Case, et al. for an ARTIFICIAL VALVE PROSTHESIS WITH IMPROVED FLOW DYNAMICS, filed on Apr. 21, 2004; the entire disclosures of which are hereby incorporated into this disclosure for the purpose of describing suitable self-expandable intraluminal medical devices for use with delivery systems described herein.

Prior to deployment, the elongate tubular member 12 is circumferentially disposed around the dilator 24, including at least a portion of the head member 34 so as to also be disposed circumferentially around the intraluminal medical device 28. The elongate tubular member 12 may be positioned about the orienting members 52, 54, if desired, until the head member 34 has been advanced through the body vessel to a position near a point of treatment. Once near the point of treatment, the elongate tubular member can be withdrawn to expose the orienting members 52, 54 but not so far as to deploy or expose the intraluminal medical device. At this point, the dilator 24, including the head member 34, can be advanced such that the now expanded orienting members 52, 54, orient themselves in the body vessel and cause the head member 34, including the intraluminal medical device 28, to rotate circumferentially within the body vessel. Alternatively, the elongate tubular member may be positioned circumferentially about the mounting region 26 while leaving the orienting members 52, 54 exposed during the entire advancement process. In this embodiment, the head member 34, and the intraluminal medical device 28, may experience rotational movement throughout all or a portion of the distance over which the dilator 24 is advanced. It is expected to be advantageous to expose the orientation member 52, 54 only during a portion of the advancement process, such as over a short distance just prior to reaching the intended point of treatment in the body vessel.

Figure 3:
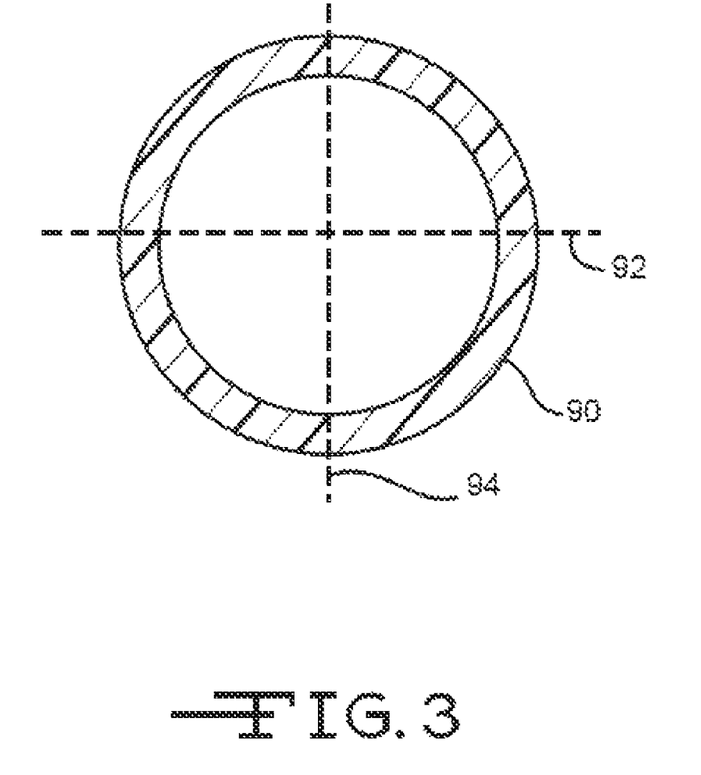
FIG. 3 is a sectional view of a body vessel within which embodiments of the invention can be used.

The delivery system 10 is used to deliver and deploy an intraluminal device 28 in a body vessel, such as the vessel 90 illustrated in FIG. 3. More specifically, the intraluminal device 28 is carried by the head member 34. However, because of the rotational connection between the head member 34 and the main body 32 of the dilator 24, the delivery system enables the intraluminal medical device 28 to be rotated to a desired orientation relative to the body vessel 30 prior to deployment of the intraluminal device 28.

Body vessels 90, being formed of soft collagenous tissues, can exhibit an irregular or oval configuration, defined by a major axis 92 and a minor axis 94, either constantly or dynamically, such as when the patient is in a supine or prone position. As mentioned above, some intraluminal medical devices may not perform as desired if the device is not oriented in a desired manner relative to the major axis 92 of the body vessel 90 following deployment. For example, some prosthetic valve devices include a valve orifice that may not function as desired if the valve orifice is oriented with its axis grossly misaligned with the major axis of the body vessel. The leaflet or leaflets of a valve device mis-oriented in this manner may be obstructed or otherwise affected by such orientation.

In an exemplary use, a user places a guidewire (not shown) in a body vessel 90 of a patient by navigating a distal end of the guidewire just beyond a point of treatment in the body vessel and leaving a proximal end of the guidewire outside of the patient. Next, with the elongate tubular member 12 disposed over the intraluminal device 28, the user advances the delivery system 10 over the previously placed guidewire by inserting the proximal end of the guidewire into the distal opening of the guidewire lumen 30 of the dilator 24. The user then advances the delivery system 10 along the path in the body vessel 90 established by the previously placed guidewire. Once the intraluminal device 28 is positioned near a desired point of treatment in the body vessel 30, the user halts the advancement of the delivery system 10. Typically, this procedure is conducted in conjunction with an imaging technique to verify positioning of the intraluminal device 28 at the desired point within the body vessel.

If the elongate tubular member 12 is positioned over the orienting members 52, 54, the user retracts the elongate tubular member 12 while maintaining the position of the dilator 24, or advances the dilator 24 while maintaining the position of the elongate tubular member 12, to expose the orienting members 52, 54 and effect their expansion. With the orienting members 52, 54 exposed and expanded, the delivery system 10 is advanced to position the intraluminal device 28 at the desired point of treatment. The act of advancing the head member 34 and the orienting members 52, 54, which are expanded against and in contact with the body vessel 90, causes the orienting members 52, 54 to follow the contour of the body vessel 90 and cause the head member 34, and thus the intraluminal medical device 28, to rotate. The advancement can be continued until the major axis 56 of the distal portion 44 of the head member 34 aligns with the major axis 92 of the body vessel 90.

Once the intraluminal medical device 28 is substantially positioned at the desired point of treatment, the user further retracts the elongate tubular member 12 while maintaining the position of the head member 34 relative to the point of treatment, or advances the dilator 24 while maintaining the position of the elongate tubular member 12. The intraluminal medical device 28 is then expanded, either simply by the act of the removal of the constraining force provided by the elongate tubular member 12 or by the input of a required external force. Once the intraluminal medical device 28 expands along its entire axial length, it is freed from its position on the mounting region 26 of the head member 34.

The intraluminal medical device 28 is thus deployed in the body vessel 90 with the desired orientation relative to the body vessel 90.

Following deployment of the intraluminal device 28, the elongate tubular member 12 and the dilator 24 are withdrawn from the body vessel 90. During this withdrawal, the orienting members 52, 54 pass through the intraluminal medical device 28. Prior to retracting the orienting members 52, 54 through the intraluminal medical device 28, the elongate tubular member 12 can be advanced over the head member 34 and the orienting members 52, 54 to prevent contact between the orienting members 52, 54 and/or the body vessel during subsequent retraction and withdrawal of the delivery system 10 from the body vessel 90.

Figure 6:
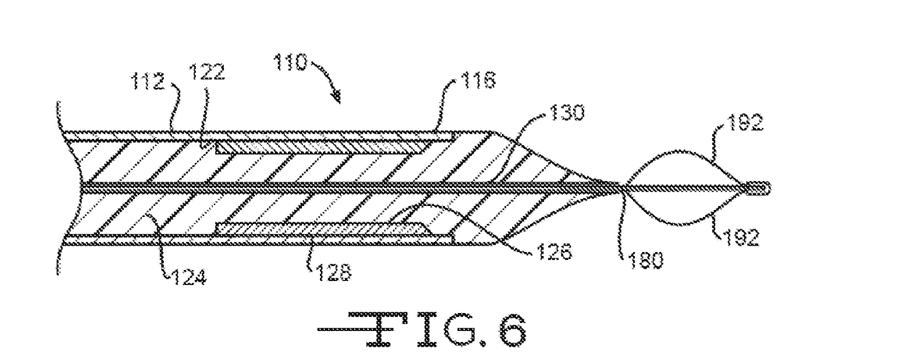
FIG. 6 is a partial sectional view of the distal end of a delivery system according to a second exemplary embodiment.
Figure 7:
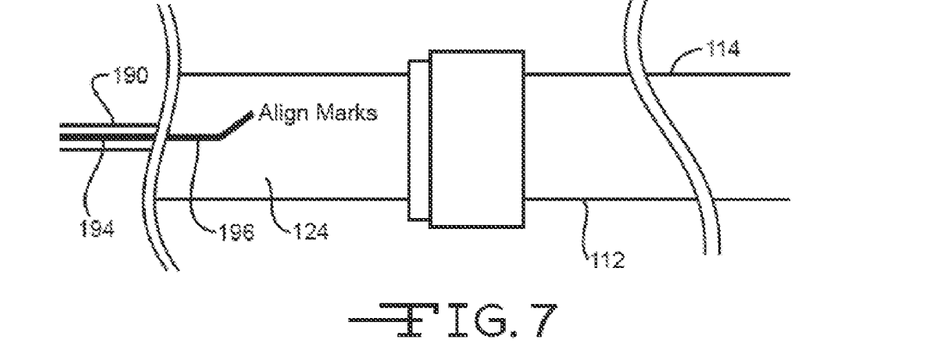
FIG. 7 is an enlarged view, partially broken away, of the proximal end of the delivery system illustrated in FIG. 6.

FIGS. 6 and 7 illustrate a delivery system 110 according to a second exemplary embodiment. This embodiment eliminates the optional rotatable head member in favor of a system of markings disposed on or otherwise associated with a functional wireguide and an elongate tubular member as described below. The delivery system 110 includes an elongate tubular member 112, such as a conventional sheath member used in delivery systems known in the art, having proximal 114 and distal ends 116. A lumen 122 extends through the elongate tubular member 112 from the proximal end 114 to the distal end 116. A dilator 124 is disposed within the lumen 122 of the elongate tubular member 112 and defines a mounting region 126 on which an expandable intraluminal medical device 128 is disposed. The elongate tubular member 112 is initially disposed over the mounting region 126 and the expandable intraluminal medical device 128 but can be retracted in a manner that exposes the intraluminal medical device 128 for deployment at a point of treatment within a body vessel.

The dilator 124 is slidably disposed within the lumen 122 of the elongate tubular member 112 and defines a wireguide lumen 130 through which a wireguide 190 can be disposed, allowing the dilator 124, and the delivery system 110, to be advanced over a wireguide that has been previously placed within a body vessel. The wireguide lumen 130 advantageously extends along the entire length of the dilator 124.

In this embodiment, the wireguide 190 includes at least one orienting member 192 extending therefrom. The at least one orienting member 192 advantageously comprises a elongate resilient member, such as a strand formed of wire, plastic or other suitable material. The wireguide 190 advantageously includes two or more orienting members 192.

The wireguide 190 includes at least one longitudinal marker 194 or other suitable indicia that is aligned on the circumference of the wireguide 190 with one of the orienting members 192. The longitudinal marker 194 can extend along any suitable length of the wireguide 190, including the entire length which is considered advantageous at least because it facilitates quality control checks during manufacturing and use, but should at least be disposed on a portion of the proximal end of the wireguide to facilitate alignment with the dilator 124, as described below.

In this embodiment, the dilator 124 includes at least one marker 196 or other suitable indicia. The expandable intraluminal medical device 128 is advantageously disposed on the dilator 124 such that a particular component or feature of the expandable intraluminal medical device 128 is aligned with the marker 196 of the dilator, similar to the alignment between a portion of the medical device and the orienting members described above in relation to the first exemplary embodiment.

The markers 194, 196 can be formed in or on their respective components, and can be formed of any suitable marker material, including conventional materials known in the art. Metallic markings, such as bismuth-and gold-based markings, are considered suitable and advantageous at least because of their wide-spread use as markers in the delivery system art as well as their acceptable visualization properties. A skilled artisan will be able to select an appropriate material based on various considerations, including desired visualization properties for the delivery system components using standard and newly-developed visualization techniques.

In use, a user advances the wireguide 190 through a body vessel, allowing the orienting member(s) 192 to orient the wireguide within the body vessel as described above in relation to the head member of the first exemplary embodiment. Once the wireguide is placed in a desired position, the user advances the delivery system 110, including the dilator 124 and elongate tubular member 112, along the path defined by the previously placed wireguide 190. Once the intraluminal medical device 128 has reached the desired point of treatment, the user rotates the dilator circumferentially about the wireguide 190 until the markers 194, 196 are aligned. The rotation transmits torque down the length of the dilator 124 and causes rotation of the expandable intraluminal medical device 128 at the point of treatment. Because of the alignment between a particular portion of the medical device 128 and the marker 196, the intraluminal medical device 128 is positioned in the vessel in a desired configuration following the rotation to align the markers 194, 196. The elongate tubular member 112 can then be retracted to effect deployment of the expandable intraluminal medical device 128 at the point of treatment in the desired configuration.

The foregoing detailed description provides exemplary embodiments of the invention and includes the best mode for practicing the invention. The description and illustration of embodiments is intended only to provide examples of the invention and not to limit the scope of the invention, or its protection, in any manner.

What is claimed is:

1. A medical device delivery system for deploying an intraluminal medical device with a body vessel, comprising:
   a dilator having a lengthwise axis and including a main body, a head member, and a rotatable connection disposed between and connecting the main body and the head member, the main body, the head member and the rotatable connection positioned on the lengthwise axis of the dilator, the main body having a first proximal end and a first distal end and the head member having a second proximal end and a second distal end, the rotatable connection connecting the first distal end and the second proximal end and enabling the head member to rotate about the lengthwise axis of the dilator independent of rotation of the main body, the second proximal end defining a mounting region and the second distal end including first and second orienting members, each of the first and second orienting members comprising a resilient member having an orienting member proximal end and an orienting member distal end attached to the second distal end and a middle portion substantially free of the second distal end, the orienting member distal end circumferentially offset from the orienting member proximal end;
   an intraluminal medical device disposed on the mounting region; and
   an elongate tubular member circumferentially disposed about the main body and at least the mounting region of the head member and the intraluminal medical device;
   wherein the first and second orienting members are opposibly positioned with respect to the lengthwise axis and extending outwardly from the head member to define a major transverse axis relative to the lengthwise axis such that the orienting members are adapted to expand against and contact a wall of said body vessel and to cause the head member and intraluminal medical device to rotate within said body vessel as said delivery system is advanced within said body vessel.

2. The medical device delivery system according to claim 1, wherein the intraluminal medical device includes a functional mechanism and wherein the intraluminal medical device is disposed on the mounting region such that at least a portion of the functional mechanism is longitudinally aligned with the at least one orienting member.

3. The medical device delivery system according to claim 2, wherein the intraluminal medical device comprises a valve device and wherein the functional mechanism comprises a valve orifice.

4. The medical device delivery system according to claim 2, wherein the intraluminal medical device comprises a stent and wherein the functional mechanism comprises a localized deposit of a bioactive agent.

5. The medical device delivery system according to claim 1, wherein the rotatable connection comprises a mating projection and socket.

6. The medical device delivery system according to claim 1, wherein the orienting member distal end of the first orienting member is circumferentially off-set from the orienting member proximal end of first orienting member by about 90 degrees.

7. The medical device delivery system according to claim 6, wherein the orienting member distal end of the second orienting member is circumferentially offset from the orienting member proximal end of second orienting member by about 90 degrees.

8. The medical device delivery system according to claim 1, wherein the first and second orienting members comprise a wire member.

9. The medical device delivery system according to claim 1, wherein the intraluminal medical device comprises a valve device.

10. The medical device delivery system according to claim 1, wherein the intraluminal medical device comprises a stent.

* * * * *